United States Patent
Riedel

(10) Patent No.: US 11,850,405 B2
(45) Date of Patent: *Dec. 26, 2023

(54) SUPPLEMENTARY DEVICES FOR ATTACHMENT TO DRUG DELIVERY DEVICES, NUMBER SLEEVE FOR DRUG DELIVERY DEVICES, AND DRUG DELIVERY DEVICES

(71) Applicant: Sanofi-Aventis Deutschland GMBH, Frankfurt am Main (DE)

(72) Inventor: Stephan Riedel, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 434 days.

This patent is subject to a terminal disclaimer.

(21) Appl. No.: 17/084,254

(22) Filed: Oct. 29, 2020

(65) Prior Publication Data

US 2021/0069423 A1 Mar. 11, 2021

Related U.S. Application Data

(62) Division of application No. 16/303,982, filed as application No. PCT/EP2017/062645 on May 24, 2017, now Pat. No. 11,123,493.

(30) Foreign Application Priority Data

May 24, 2016 (EP) .................................. 16171083

(51) Int. Cl.
*A61M 5/315* (2006.01)
*G16H 20/17* (2018.01)
(Continued)

(52) U.S. Cl.
CPC .... *A61M 5/31535* (2013.01); *A61M 5/31551* (2013.01); *G16H 20/10* (2018.01);
(Continued)

(58) Field of Classification Search
CPC .......... A61M 5/31525; A61M 5/31533; A61M 5/31551
See application file for complete search history.

(56) References Cited

U.S. PATENT DOCUMENTS 9,101,721 B2 8/2015 Butler et al.
11,123,493 B2 * 9/2021 Riedel ............... A61M 5/31535
(Continued)

FOREIGN PATENT DOCUMENTS

| CN | 102458533 | 5/2012 |
| CN | 103797336 | 5/2014 |

(Continued)

OTHER PUBLICATIONS

PCT International Preliminary Report on Patentability in Appln. No. PCT/EP2017/062645, dated Nov. 27, 2018, 10 pages.
(Continued)

*Primary Examiner* — Laura A Bouchelle
(74) *Attorney, Agent, or Firm* — Fish & Richardson P.C.

(57) ABSTRACT

A supplementary device for attachment to a drug delivery device is provided. The device includes an attachment mechanism for coupling the supplementary device to the drug delivery device, an imaging arrangement for providing image data representing a captured image of one or more numbers present on a number sleeve of the drug delivery device and a processor arrangement. The processor arrangement is configured to receive the image data; perform optical character recognition on the image data to determine a quantity of a currently set dose of medicament; cause display of the quantity of the currently set dose; process the (Continued)

image data to identify one or more characteristics of the number sleeve; determine from the identified characteristics whether the currently set dose is a permitted dose; and if the currently set dose is not a permitted dose, cause an indication that the currently set dose is not a permitted dose.

16 Claims, 7 Drawing Sheets

(51) Int. Cl.
    *G16H 20/10*     (2018.01)
    *A61M 5/31*     (2006.01)

(52) U.S. Cl.
    CPC ..... *G16H 20/17* (2018.01); *A61M 2005/3126* (2013.01); *A61M 2205/3569* (2013.01); *A61M 2205/502* (2013.01); *A61M 2205/52* (2013.01); *A61M 2205/581* (2013.01); *A61M 2205/584* (2013.01); *A61M 2205/6081* (2013.01)

(56) References Cited

U.S. PATENT DOCUMENTS

2005/0171476 A1     8/2005     Judson et al.
2013/0289518 A1*   10/2013     Butler ............... A61M 5/31585
                                                604/207

FOREIGN PATENT DOCUMENTS

| | | | | |
|---|---|---|---|---|
| CN | 104519931 | 4/2015 | | |
| JP | 2003-010327 | 1/2003 | | |
| JP | 2006-520949 | 9/2006 | | |
| JP | 2013-521963 | 6/2013 | | |
| JP | 2013-539699 | 10/2013 | | |
| JP | 2014-158834 | 9/2014 | | |
| JP | 2014-533539 | 12/2014 | | |
| WO | WO 2010/139644 | 12/2010 | | |
| WO | WO 2011/117212 | 9/2011 | | |
| WO | WO 2013/010887 | 1/2013 | | |
| WO | WO 2013/116353 | 8/2013 | | |
| WO | WO 2013/120774 | 8/2013 | | |
| WO | WO 2013/120775 | 8/2013 | | |
| WO | WO 2014/023763 | 2/2014 | | |
| WO | WO 2014/064691 | 5/2014 | | |
| WO | WO-2014111340 A1 * | 7/2014 | .............. | A61M 5/20 |
| WO | WO-2014139917 A1 * | 9/2014 | .......... | A61M 5/3146 |
| WO | WO 2014/173773 | 10/2014 | | |
| WO | WO 2015/007809 | 1/2015 | | |
| WO | 105120929 | 12/2015 | | |
| WO | WO 2016/062604 | 4/2016 | | |
| WO | WO 2016/062605 | 4/2016 | | |
| WO | WO 2013/076026 | 5/2020 | | |

OTHER PUBLICATIONS

PCT International Search Report and Written Opinion in Appln. No. PCT/EP2017/062645, dated Oct. 13, 2017, 16 pages.

* cited by examiner

SUPPLEMENTARY DEVICES FOR ATTACHMENT TO DRUG DELIVERY DEVICES, NUMBER SLEEVE FOR DRUG DELIVERY DEVICES, AND DRUG DELIVERY DEVICES

CROSS REFERENCE TO RELATED APPLICATIONS

The present application is divisional of U.S. patent application Ser. No. 16/303,982, filed Nov. 21, 2018, which is the national stage entry of International Patent Application No. PCT/EP2017/062645, filed on May 24, 2017, and claims priority to Application No. EP 16171083.5, filed in on May 24, 2016, the disclosures of which are incorporated herein by reference.

TECHNICAL FIELD

The present disclosure relates to a supplementary device for attachment to a drug delivery device, wherein the supplementary device comprises an imaging arrangement and a processor arrangement configured to calculate a quantity of a currently set dose of medicament. The present disclosure relates also to a number sleeve for a drug delivery device and to a drug delivery device including such.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty drug or medicament cartridge by a new one. Either pen may come with a set of one-way needles that are replaced before each use. The insulin dose to be injected can then for instance be manually selected at the insulin pen by turning a dosage knob and observing the set dose shown on part of a number sleeve that is visible through a dose window of the insulin pen. In other cases, the set dose is show on an electronic display of the insulin pen. The dose is then injected by inserting the needle into a suitable skin portion and pressing an injection button of the insulin pen.

To be able to monitor insulin injection, for instance to prevent false handling of the insulin pen or to keep track of the doses already applied, it is desirable to measure information related to a condition and/or use of the injection device, such as for instance information on the injected insulin type and dose.

SUMMARY

At least one aspect of the present disclosure provides a supplementary device for attachment to a drug delivery device. The supplementary device includes an attachment mechanism for coupling the supplementary device to the drug delivery device; an imaging arrangement configured to provide image data representing a captured image of one or more numbers present on a number sleeve of the drug delivery device at a location on the number sleeve corresponding to a currently set dose of medicament; and a processor arrangement. The processor arrangement is configured to: receive the image data representing the captured image; perform optical character recognition on the image data to determine a quantity of the currently set dose of medicament; cause display of the quantity of the currently set dose of medicament; process the image data representing the captured image to identify one or more characteristics of the number sleeve at the location; determine from the determined characteristics of the number sleeve whether the currently set dose of drug is a permitted dose; and in response to determining that the currently set dose of drug is not a permitted dose, cause an indication that the currently set dose of drug is not a permitted dose to be provided.

This supplementary device may allow a user easily to identify whether a currently set dose is a dose that is permitted for the user, even if they are unable to determine that information directly from the drug delivery device. This can improve usablility, and also safety, for the user. Moreover, this can be achieved in an intuitive way, according to various optional features which are described below.

The processor arrangement may be configured to process the image data representing the captured image to identify one or more characteristics of the number sleeve at the location by determining a colour of the background of the number sleeve at the location.

The processor arrangement may be configured to process the image data representing the captured image to identify one or more characteristics of the number sleeve at the location by determining a colour of the numbers on the number sleeve at the location.

The processor arrangement may be configured to determine from the determined characteristics of the number sleeve whether the currently set dose of drug is a permitted dose by determining whether the characteristics of the number sleeve at the location are light coloured numbers on a dark coloured background.

The processor arrangement may be configured to determine from the determined characteristics of the number sleeve whether the currently set dose of drug is a permitted dose by determining whether the characteristics of the number sleeve at the location are dark coloured numbers on a light coloured background.

The processor arrangement may be configured to cause the indication that the currently set dose of drug is not a permitted dose to be provided by causing display of a message.

The processor arrangement may be configured to cause the indication that the currently set dose of drug is not a permitted dose to be provided by causing display of a message simultaneously with causing display of the quantity of the currently set dose of medicament.

The processor arrangement may be configured to cause the indication that the currently set dose of drug is not a permitted dose to be provided by causing display of a message alternately with causing display of the quantity of the currently set dose of medicament.

The processor arrangement may be configured to cause the indication that the currently set dose of drug is not a permitted dose to be provided by causing illumination of an LED or other optical transducer.

The processor arrangement may be configured, in response to determining that the currently set dose of drug is not a permitted dose, to actuate a locking arrangement to prevent drug delivery.

Certain aspects of the present disclosure provides a system comprising the supplementary device above and a drug delivery device having a number sleeve with numbers provided thereon.

Certain aspects of the present disclosure provides a number sleeve for a drug administration device, the number sleeve comprising a generally cylindrical outer surface on which are provided a sequence of numbers arranged at different locations on the surface with the sequence provided in a helix, each of the numbers relating to a drug dose, where the surface at locations corresponding to doses within a specific dose range has different characteristics to the surface at locations corresponding to doses that are outside of the specific dose range.

Through these features, a supplementary device may be able to determine from viewing the number sleeve not only a currently dialled or set dose but also whether the currently dialled or set dose is one that is permitted to be delivered to the user. This does not require the supplementary device to be pre-programmed with information relating to permitted dose sizes for the user. Also through these features, a user may be able to determine from observing a drug delivery device including the number sleeve not only a currently set or dialled dose but and whether the set or dialled dose is within a range of doses that are permitted for the user by their drug administration plan or regime.

The different characteristics may be different colours for the numbers on the surface of the number sleeve.

The different characteristics may be different colours for a background to the numbers on the surface of the number sleeve.

The different colours may be detectable by the human eye.

The surface at locations corresponding to doses within the specific range may indicate the dose as a number that is coloured black on a white background, and the surface at locations corresponding to doses outside the specific range may indicate the dose as a number that is coloured white on a black background.

Another aspect of the disclosure provides a drug delivery device including the number sleeve above.

BRIEF DESCRIPTION OF THE FIGURES

Embodiments of the disclosure will now be described, by way of example, with reference to the accompanying drawings, in which:

FIG. 1b is a perspective view of some detail of the drug delivery device of FIG. 1a;

DETAILED DESCRIPTION

In brief, the disclosure describes a supplementary device (alternatively known as a companion device, a clip-on device or a sensor device) that is operable with drug delivery device, e.g. an injection device, such as a pen injector. The supplementary device is configured to view a number sleeve of the drug delivery device and determine therefrom a set drug dose, and also a delivered dose. The supplementary device is configured also to detect from the number sleeve whether a currently dialled dose is a dose that is indicated by the drug delivery device to be a permitted dose. This is indicated by the number sleeve of the drug delivery device, and not by the numbers that are present on the number sleeve at a location that is being viewed but by some other optical characteristic of the number sleeve. In some embodiments, the currently set dose being a permitted dose is indicated by the numbers being provided as black numerals on a white background and the currently set dose not being a permitted dose is indicated by the numbers being provided as white numerals on a black background. The supplementary device is configured to respond to a detection of a currently set dose not being a permitted dose by providing an indication to a user, for instance in the form of a message. The supplementary device may also act to prevent drug delivery unless the set dose is a permitted dose.

The disclosure also describes a number sleeve for a drug delivery device, and a drug delivery device including the number sleeve. The number sleeve is provided with different characteristics at different locations, where locations corresponding to a dose in a specific dose range, corresponding to permitted doses, have a first characteristic and locations corresponding to a dose that are not in the permitted dose range have a second characteristic. These characteristics allow a supplementary device to sense from the drug administration device whether the dialled dose is a permitted dose even if the supplementary device does not have any pre-existing information about which doses are permitted for the user. These characteristics also allow a user easily to see from the injection device 1, when the supplementary device 2 is not in place (e.g. when not in use), whether the currently set or dialled dose is permitted. In some embodiments, locations corresponding to a dose which is permitted indicate the dose as a number that is coloured black on a white background, and locations corresponding to a dose that is not permitted are indicated by a number that is coloured white on a black background.

In the following, embodiments of the present disclosure will be described with reference to an insulin injection device. The present disclosure is however not limited to such application and may equally well be deployed with injection devices that eject other medicaments, or with other types of drug delivery device.

Figure 1A:
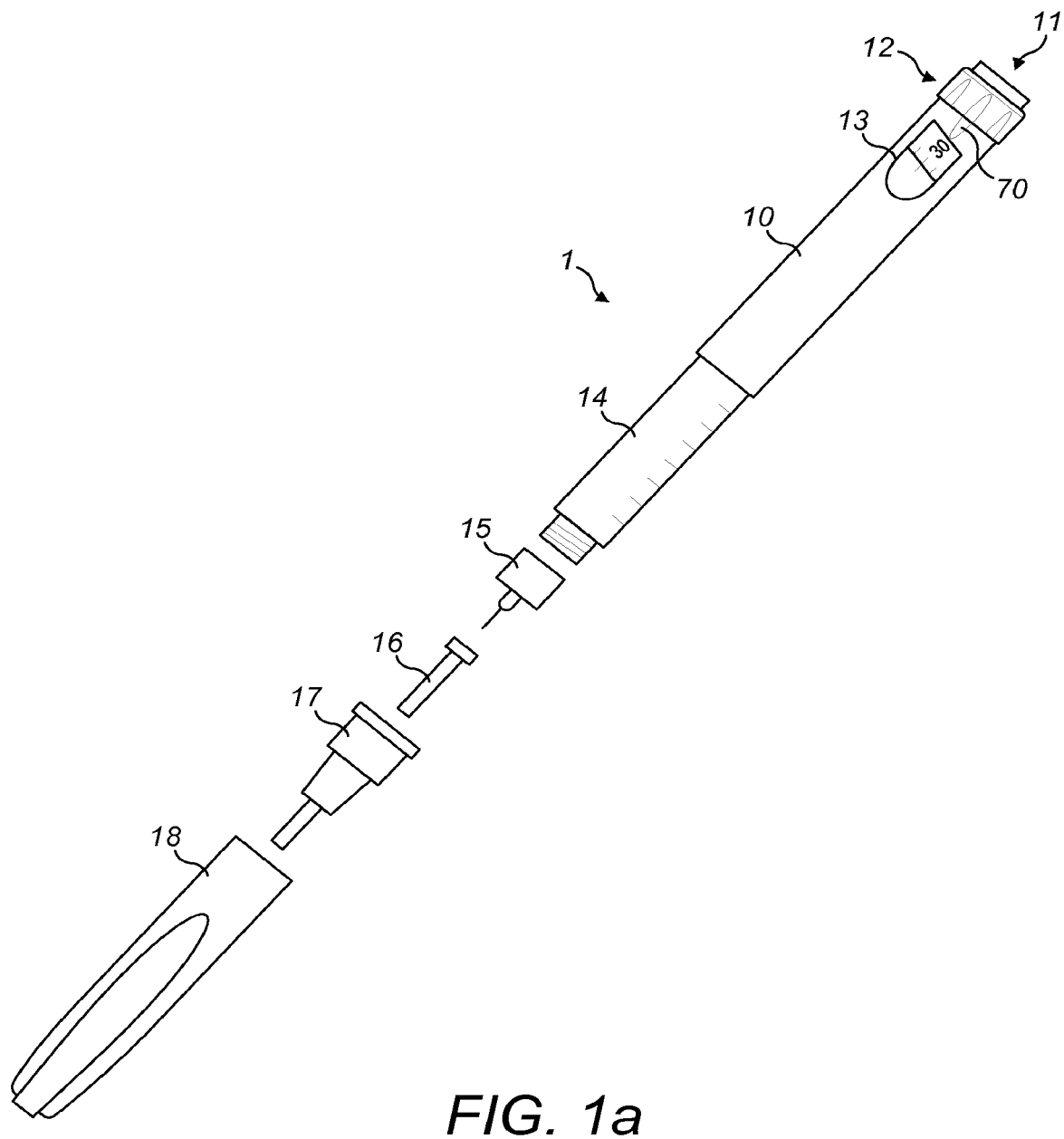
FIG. 1a is an exploded view of an drug delivery device according to exemplary embodiments.

FIG. 1 is an exploded view of an injection device 1, which may for instance represent Sanofi's Solostar® insulin injection pen. More generally, it is a pen-type injector device.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently. A label (not shown) is provided on the housing 10. The label includes information about the drug included within the injection device, including information identifying the medicament. The information identifying the drug may be in the form of text. The information identifying the drug may also be in the form of a colour. The information identifying the drug may also be encoded into a barcode, QR code or the like. The information identifying the drug may also be in the form of a black and white pattern, a colour pattern or shading.

Turning the dosage knob 12 causes a mechanical click sound to provide acoustical feedback to a user. The numbers displayed in dosage window 13, in the sense that they are visible through the dosage window 13, are present on a number sleeve 19. The numbers are for instance provided on the number sleeve 19 by printing. As can be seen best from FIGS. 7 and 8, the numbers are provided in a continuous sequence on the number sleeve 19. Individual numbers (including numbers formed from two characters) are formed at consecutive locations in the shape of a helix around a generally cylindrical outer surface of the number sleeve 19.

The number sleeve 19 is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
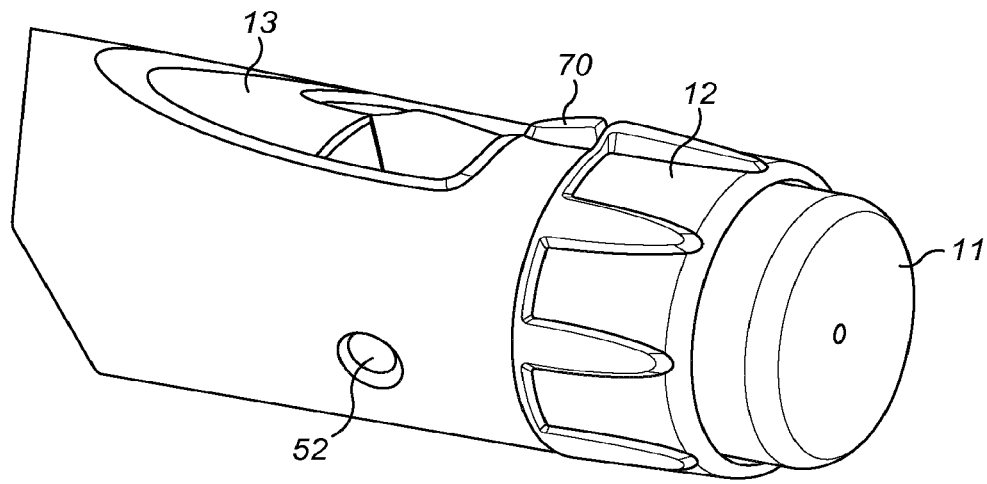

FIG. 1b is a close-up of the end of the injection device 1. This Fig. shows a locating rib 70 that is located between the viewing window 13 and the dosage knob 12.

Figure 2A:
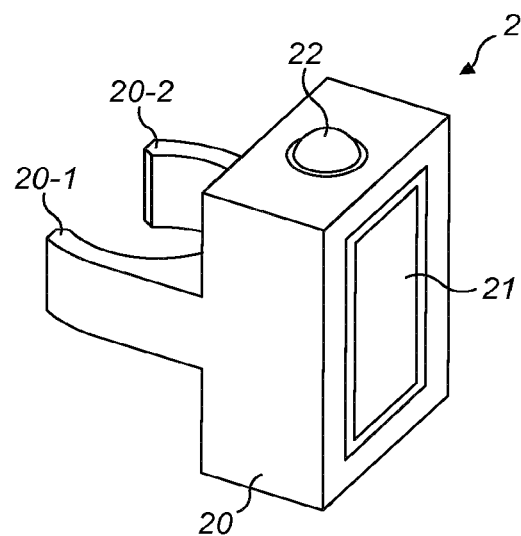
FIG. 2a is a schematic illustration of a supplementary device according to exemplary embodiments that can be releasably attached to the drug delivery device of FIGS. 1a and 1b.

FIG. 2a is a schematic illustration of an embodiment of a supplementary device 2 to be releasably attached to injection device 1 of FIG. 1. Supplementary device 2 comprises a housing 20 with a mating unit or attachment mechanism configured and embrace the housing 10 of injection device 1 of FIG. 1, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage window 13 of injection device 1 is obstructed by supplementary device 2 when attached to injection device 1.

Supplementary device 2 further comprises at least one user input transducer, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
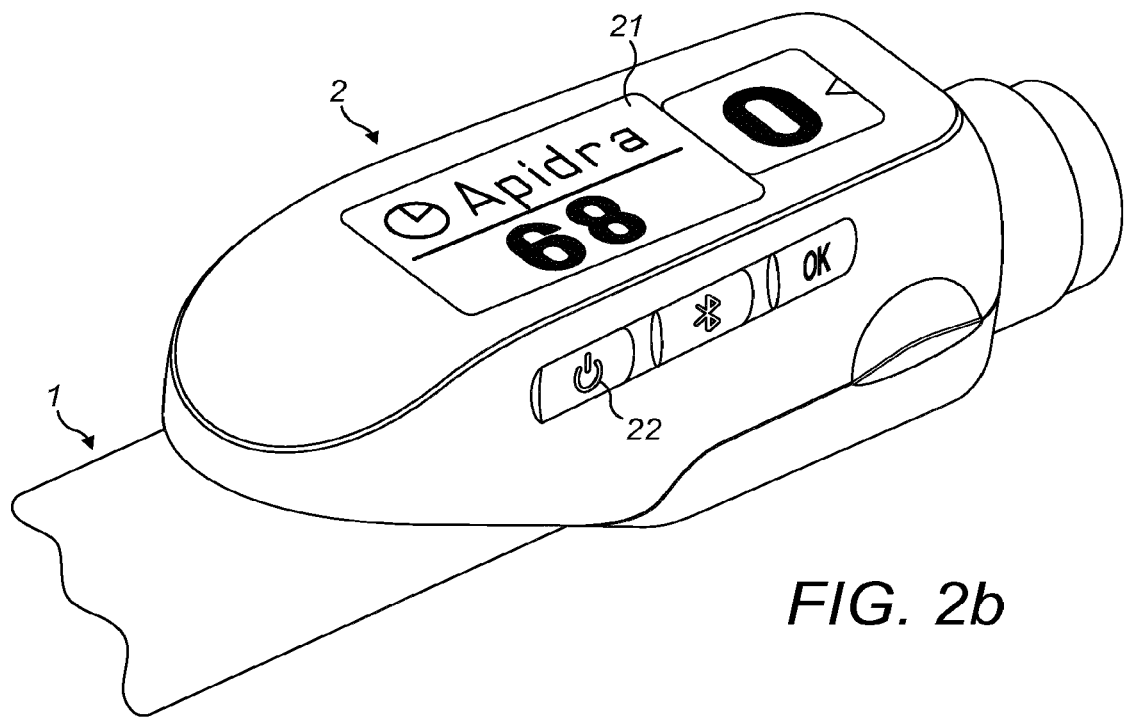
FIG. 2b is an isometric view of another supplementary device according to exemplary embodiments that can be releasably attached to the drug delivery device of FIGS. 1a and 1b.

FIG. 2b is a schematic illustration of a second embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22, 33, 34 allow a user to turn on/off supplementary device 2, to trigger actions (for instance to cause establishment of a connection to or a pairing with another device, and/or to trigger transmission of information from supplementary device 2 to another device), or to confirm something.

Figure 2C:
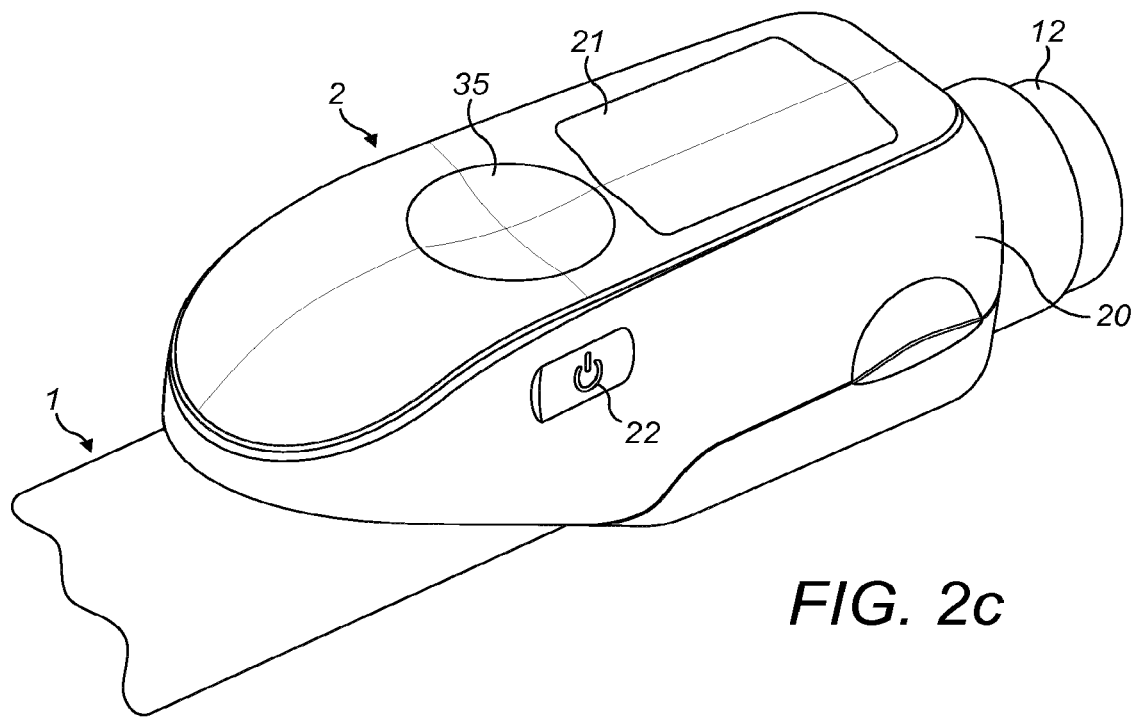
FIG. 2c is an isometric view of yet another supplementary device according to exemplary embodiments that can be releasably attached to the drug delivery device of FIGS. 1a and 1b.

FIG. 2c is a schematic illustration of a third embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3:
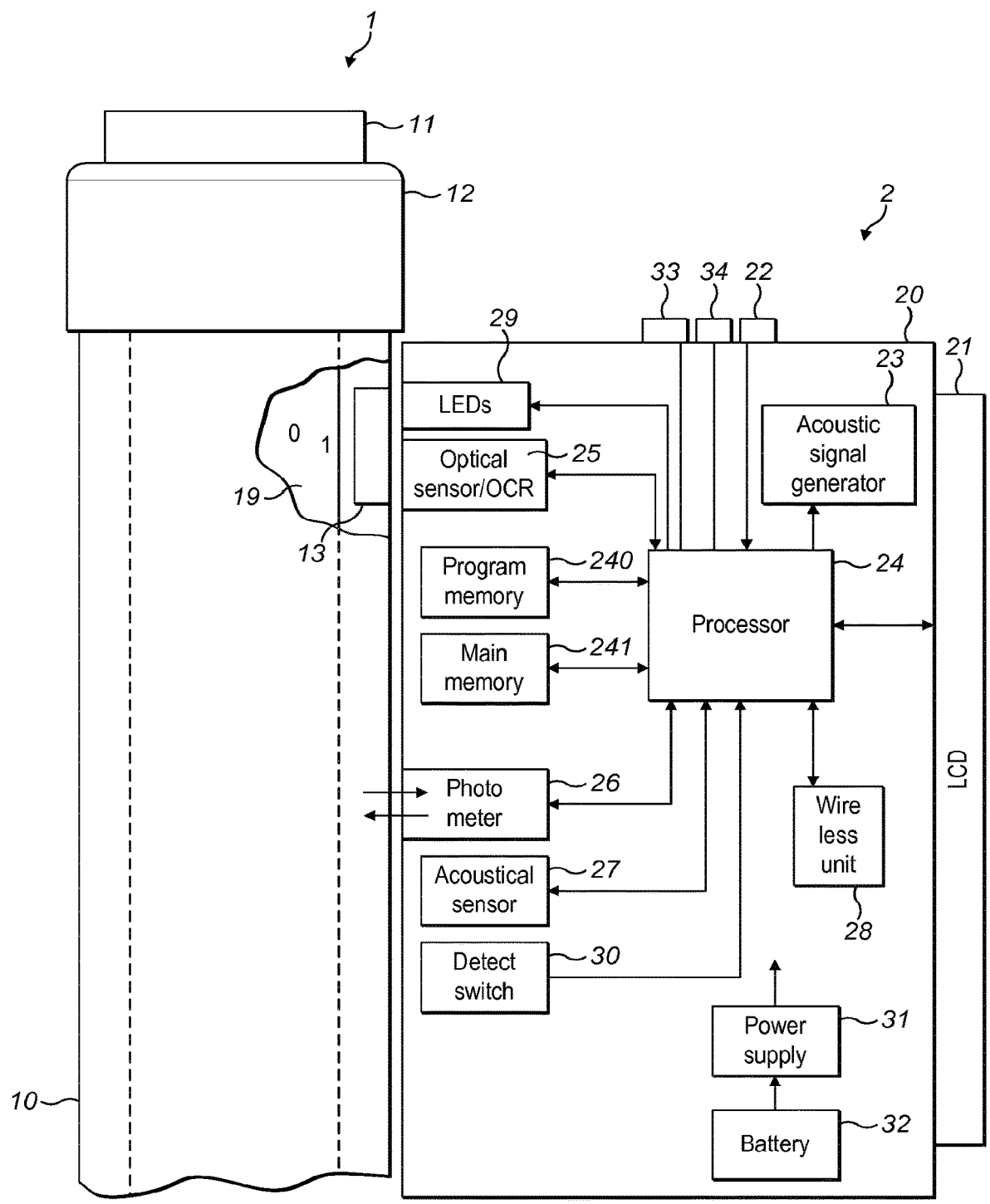
FIG. 3 is a schematic view of the FIGS. 2c, 2b and 2c supplementary devices attached to a drug delivery device according to exemplary embodiments and showing components of the supplementary device.

FIG. 3 shows a schematic view of the supplementary device 2 of FIG. 2a in a state where it is attached to injection device 1 of FIG. 1.

With the housing 20 of supplementary device 2, a plurality of components are contained. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed. The dose is displayed by way of numbers present on the number sleeve 19 contained in injection device 1, which numbers are visible through the dosage window 13. Optical sensor/OCR reader 25 is further capable of recognizing characters (e.g. numbers) from the captured image and to provide this information to processor 24. In this case, the optical sensor/OCR reader 25 includes a processor arrangement that is programmed by software stored in memory to be configured to perform optical character recognition. Alternatively, unit 25 in supplementary device 2 may only be an optical sensor, e.g. a camera, for capturing images and providing information on the captured images to processor 24. Then processor 24 provides the function of performing OCR on the captured images.

The optical sensor 25 or the processor 24 provides the function also of detecting whether characteristics of the number sleeve 19 at the location being viewed by the optical sensor indicate whether or not the set or dialled dose is permitted.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens system, for instance including two aspheric lenses. The magnification ratio (image size to object size ratio) may be smaller than 1. The magnification ratio may be in the range of 0.05 to 0.5. In one embodiment the magnification ration may be 0.15.

Processor 24 further controls a photometer 26, that is configured to determine an optical property of the housing 10 of injection device 1, for example a colour or a shading. The optical property may only be present in a specific portion of housing 10, for example an insulin container comprised within injection device 1, which colour or colour coding may for instance be visible through a further window in housing 10 (and/or in number sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing or insulin container may then be provided to processor 24 to determine the colour of the housing or insulin container by way of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage window 13, are avoided or reduced.

Processor 24 further controls (and/or receives signals from) an acoustic sensor 27, which is configured to sense sounds produced by injection device 1. Such sounds may for instance occur when a dose is dialled by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1. A battery 32 powers the processor 24 and other components by way of a power supply 31.

The supplementary device 2 of FIG. 3 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

Figure 4:
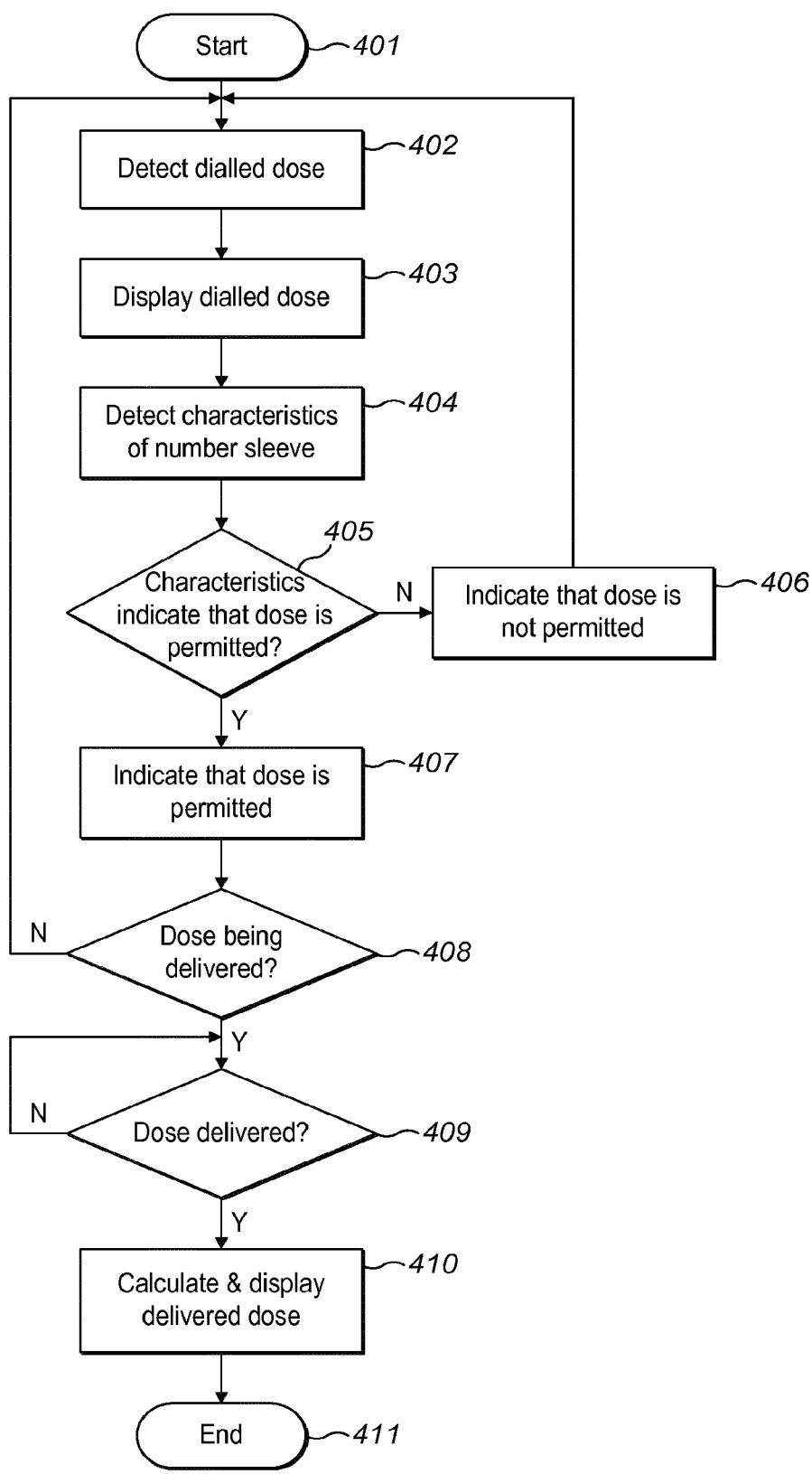
FIG. 4 is a flowchart illustrating exemplary operation of the supplementary device according to exemplary embodiments.

FIG. 4 is a flow chart illustrating operation of the supplementary device 2. It will be appreciated that FIG. 4 is schematic, and omits many of the low level details of operation of the supplementary device.

The operation starts at step 401. At step 402, the supplementary device 2 detects the dose that is dialled into, or set in (these terms are used interchangeably), the injection device 1. The dialled dose is detected by performing optical character recognition on the image that is provided by the optical sensor 25, which is directed to read the number sleeve 19 of the injection device 1 at the location of the dosage window 13, as described above. Initially, the dialled dose typically is 0, before the user operates the injection device 1. Following step 402, the dialled dose is displayed in step 403 on the display 21. In this way, the user is able to determine the dose that is dialled into the injection device 1 even though they are unable to view directly the number sleeve 19 through the dosage window 13.

At step 404, the supplementary device detects characteristics of the number sleeve 19. The characteristic detected at step 404 are not the numbers that are present on the number sleeve 19, but are some other characteristics.

The number sleeve 19 of the injection device 1 is provided with different characteristics at different locations, where locations corresponding to a dose that is permitted have a first characteristic and locations corresponding to a dose that are not permitted have a second characteristic. In some embodiments, as shown in FIGS. 5A, 5B, 6, 7 and 8, locations corresponding to a dose which is in a permitted range of doses indicate the dose as a number that is coloured black on a white background, and locations corresponding to a dose that is not permitted are indicated by a number that is coloured white on a black background. These characteristics allow a user easily to see from the injection device 1, when the supplementary device 2 is not in place, whether the currently set or dialled dose is permitted.

Figure 5A:
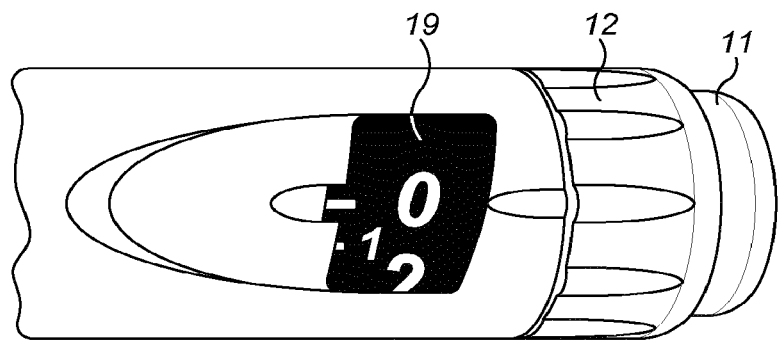
FIGS. 5A and 5B are views of a drug delivery device according to exemplary embodiments showing the number sleeve at different dialled doses.
Figure 5B:
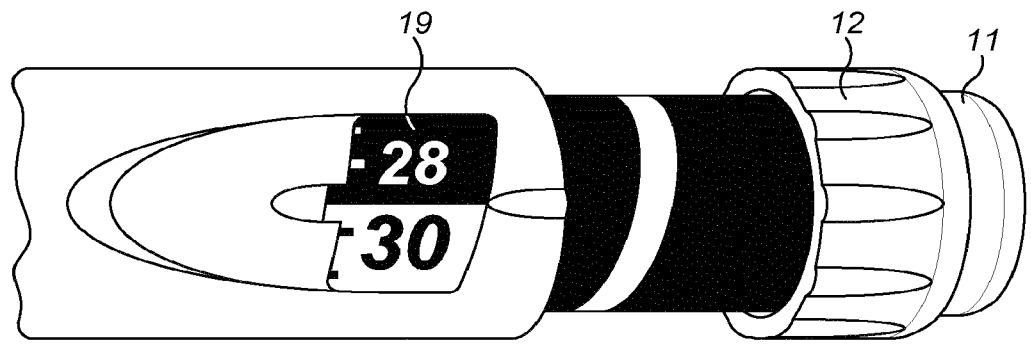

In the FIGS. 5A and 5B injection device 1, the number sleeve 19 is marked to indicate that doses of 30 and higher are permitted. The whole of the number sleeve 19 of this injection device 1 is shown in FIG. 7.

Figure 7:
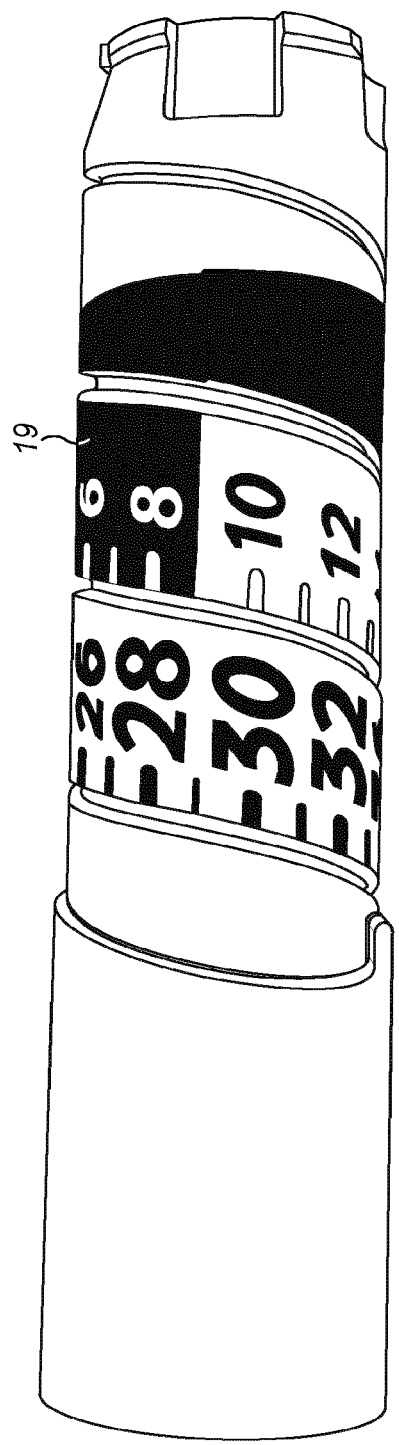
FIG. 7 is a view of a number sleeve according to exemplary embodiments that forms part of the drug delivery device of FIGS. 1a and 1b.

As can be seen in particular from FIG. 7, locations corresponding to doses of 30 and above indicate the dose as a number that is coloured black on a white background. Locations corresponding to doses between 0 and 29 are indicated by a number that is coloured white on a black background.

Figure 6:
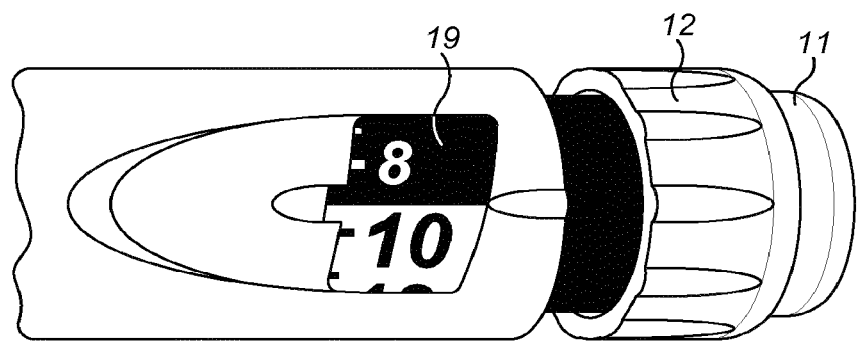
FIG. 6 is a view of a different drug delivery device according to exemplary embodiments showing the number sleeve according to exemplary embodiments at a certain dialled dose.

In the FIG. 6 injection device 1, the number sleeve 19 is marked to indicate that doses of 10 and higher value are permitted. The whole of the number sleeve 19 of this injection device 1 is shown in FIG. 8.

Figure 8:
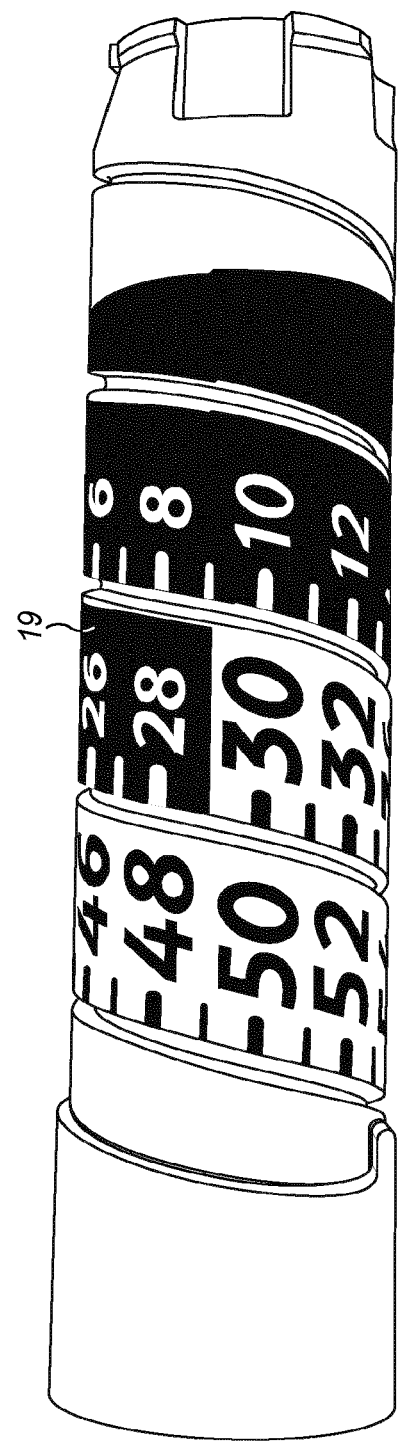
FIG. 8 is a view of another number sleeve according to exemplary embodiments that forms part of the drug delivery device of FIGS. 1a and 1b.

As can be seen in particular from FIG. 8, locations corresponding to doses of 10 and above indicate the dose as a number that is coloured black on a white background. Locations corresponding to doses between 0 and 9 are indicated by a number that is coloured white on a black background.

In addition to the colour scheme described above, the number sleeve 19 is marked to indicate that doses of 30 and higher value are permitted by the size of the numbers, i.e. the font size. The feature of font size can be used in combination with the colour scheme feature, as can be seen in FIG. 8 for example. However, it is immanently clear to the skilled person that each feature—font size, colour scheme—can also be used alone, i.e. independently of the other.

When the supplementary device 2 is installed on the injection device 1, the user is unable to see the number sleeve 19, or at least is unable to see the part of the number sleeve that is coincident with the dosage window 13. However, the supplementary device 2 is able to detect the characteristics of the number sleeve 19 by examining the output of the optical sensor/OCR 25. The determination of the characteristics may be performed as part of the processing of the optical sensor/OCR 25 output when performing optical character recognition, or it may be performed as a separate step.

After the characteristics of the number sleeve 19 at the location currently being viewed by the optical sensor 25 have been detected, at step 405 it is determined by supplementary device 2 whether the characteristics indicate that the currently set dose is permitted. In the event that step 405 provides a negative response, because the number on the number sleeve 19 is provided in the colour white on a black background, the operation proceeds to step 406. Here, the supplementary device 406 indicates that the currently set dose is not permitted. The indication may be provided in one of a number of manners which are described below.

After step 406, the operation returns to step 402. Here, the dialled dose is again detected, before the dose is then displayed at step 403. Afterwards, the characteristics of the number sleeve 19 are again detected at step 404 and a determination as to whether the characteristics indicate that the dose is permitted is performed at step 405. This loop continues until it is detected at step 405 that the dose is permitted, when the operation proceeds to step 407. In this way, the user is continually provided with an indication that the dose is not permitted until such time that the supplementary device 2 determines that the currently set dose is permitted.

At step 407, the supplementary device 2 indicates to the user that the dose that is set in the injection device 1 is permitted. Indication may be provided, for instance, by way of a suitable message on the display 21. The indication may be by way of refraining from providing an indication that the dose is not permitted. In particular, if the currently dialled dose is not permitted, a warning message may be provided, with the warning message being removed once the supplementary device 2 detects that the currently set dose is permitted. The indication may be instead provided by an LED or other small optical output transducer. The indication may for instance be in the form of a green light.

After step 407, the supplementary device 2 determines that step 408 whether the dose is being delivered. This determination may be made in any suitable way, as is known in the art. On a positive determination, the operation proceeds at step 409, where it is determined whether the dose has been delivered. This may be performed in any suitable way, as is known in the art. The operation remains at step 409 until it is determined that the dose has been delivered, when the operation proceeds to step 410.

At step 401, the delivered dose is calculated and displayed on the display 21. This may be performed in any suitable way, as is known in the art. The calculation of the delivered dose may involve subtracting the dose that was set into the injection device 1, following dose delivery from the dose that was set in the injection 1 before dose delivery. If all of the set dose was delivered, then the remaining dose is 0 and the delivered dose is equal to the set dose.

Following step 410, the operation ends at step 411.

If at step 408, the supplementary device 2 determines that the dose is not being delivered, the operation returns to step 402, where the dialled dose is again detected. This loop ensures that the dialled dose is detected and displayed up until the dose is delivered. It also ensures that the supplementary device 2 either indicates at step 406 that the dose is not permitted or indicates that step 407 that the dose is permitted, based on the detected characteristics of the number sleeve 19, up until the dose is delivered. This occurs regardless of the value of the dose that is set in the injection device 1. Indeed, the supplementary device 2 does not need to be aware of the range of doses that are permitted by the injection device 1. Instead, the supplementary device 2 only needs to determine the characteristics of the number sleeve 19 at the location that is being viewed by the optical sensor 25 in order to determine whether the dose is permitted.

In the above, the detection as to whether a dose is permitted is carried out by detecting whether the numbers on the number sleeve 19 are provided in white-on-black or in black-on-white. In other embodiments, the determination is made based on some other characteristic of the numbers on the number sleeve 19. For instance, the numbers on the number sleeve 19 indicates doses in the range that is permitted may have a different colour to numbers in the range that is not permitted but the background remains the same colour in both cases. For instance, the background of the number sleeve 19 may be white for the entire range of doses that can be delivered by the injection device 1, and the numbers are provided in a first colour (for instance grey or black) when the number relates to a dose that is permitted and in a different colour (for instance red or orange) when the number relates to a dose that is not permitted. In this case, step 404 of FIG. 4 involves the supplementary device to detecting from signals provided by the optical sensor 25 what colour are the numbers on the number sleeve 19 and/or what colour is the background at the location currently being viewed by the optical sensor 25. Colour determination may be in terms solely of whether the numbers are relatively light or relatively dark in colour, and/or whether the background is relatively light or relatively dark in colour.

In some embodiments, the colour of the numbers is the same for all numbers on the number sleeve 19, but the colour of the background of the number sleeve 19 changes depending on whether the number at the particular location relates to a dose that is permitted. For instance, the numbers on the number sleeve 19 may be a first colour (for instance grey or black) for all values, and the background may be a first colour (e.g. yellow or white) for values of a dose that are permitted and a second colour (e.g. orange or red) for dose values that are not permitted. In this case, the detection of the characteristics of the number sleeve 19 at step 404 involves detecting a background colour of the number sleeve 19 and step 405 involves determining whether the background colour indicates whether the dose is permitted. Having a red or orange colour as the colour of the background of the number sleeve 19 for doses that are not permitted means that the user can easily determine from examination of the number sleeve 19 of the injection device when the supplementary device 2 is not installed whether the currently set does is a permitted dose.

In some embodiments, the background of the number sleeve 19 is provided with a pattern, for instance a striped pattern, at locations corresponding to a dose that is not permitted and is provided with an un-patterned background at locations corresponding to a dose that is permitted. In some embodiments, the converse is true, so that a patterned background is provided at locations corresponding to doses that are permitted.

In some embodiments, the characteristics of the number sleeve 19 are different at different locations in a way that is detectable by the optical detector 25 but that is not detectable by human users. For instance, the number sleeve 19 is provided with a marking that is visible in ultraviolet or infrared. Either the marking is different at locations on a number sleeve 19 corresponding to doses that are permitted compared to the markings that locations on the number sleeve 19 where doses are not permitted, or vice versa. With these embodiments, supplementary device 2 is able to determine from processing of signals provided by the optical sensor whether a dose that is currently set is permitted, but a user viewing the injection device 1 when the supplementary device is not installed would not be able to determine from characteristics of the number sleeve 19 whether the currently set dose was permitted.

The indication that the dose is not permitted that is provided at step 406 may be provided on the display 21, or it may be provided in some other way. As regards the display 21, the indication may be provided as a message that is displayed on the display 21. The message may take the form "dose not permitted", or some other suitable form. The indication may be provided continually. For instance, one part of the display may be used to include the indication that the dose is not permitted and another part of the display may be used to indicate the set dose. Alternatively, the indication may be provided intermittently, for instance, the display 21 may be caused to alternate between displaying the dialled dose and displaying a message that the dose is not permitted.

Alternatively, the indication may be by way of a separate transducer, for instance an LED or other small optical transducer. The indication that the dose is not permitted may be of a colour that is traditionally associated with 'stop', or an alert, for instance, the colour red or the colour orange. For instance, the indication may be made by way of a small red LED or other red optical transducer.

Alternatively or in addition, the indication may be made acoustically, for instance by way of a buzzer. Alternatively, the indication may be made haptically. In some embodiments, the supplementary device 2 is configured to monitor whether the characteristics of the number sleeve 19 that indicate that the doses permitted have been detected after the operation starts at step 401. In these embodiments, the supplementary device 2 is configured to indicate, for instance on the display 21, whether the user needs to increase or decrease the currently dialled dose in order to reach a dose that is permitted. After starting, the dialled dose is smaller than the lower limit of the range of doses that is permitted. As such, until the supplementary device 2 detects that the characteristics of the number sleeve 19 viewed by the optical sensor 25 indicate that the currently dialled dose is permitted, the supplementary device 2 indicates to the user that the dose needs to be increased. This can occur for example by providing an arrow pointing upwards on the display 21. It can occur alternatively by providing a message "increase dose" on the display 21. Such a message also constitutes an indication that the currently dialled dose is not permitted.

When the currently dialled dose is a permitted dose, no indications that the dose is not permitted are provided. If the user operates the injection device 1 such that the currently dialled dose exceeds the upper limit of the range that is permitted, as detected by the supplementary device from the characteristics of the number sleeve 19 at step 404, the supplementary device 2 may indicate to the user that the dialled dose needs to be reduced. This can occur for instance by causing display on the display 21 of a downwardly pointing arrow or a message stating "decrease dose", or such like.

It will be appreciated that the supplementary device 2 does not need to be provided with information indicating the range of doses that are permitted in order to provide this function. Instead, the supplementary device 2 can determine whether to provide an increase dose message or a decrease dose message firstly by determining whether the currently dialled dose has yet given rise to detecting characteristics of the number sleeve 19 indicating that the dose is permitted, and after the characteristics indicate that the dose is permitted by responding to detection that the characteristics of the number sleeve 19 indicate that the dose is not permitted by determining whether the dialled dose has increased or decreased since the dose dialled at the time when the characteristics on the number sleeve 19 were detected to indicate that the dose is permitted.

In some embodiments, the supplementary device 2 is configured such that it is unable to detect the dose except when the characteristics indicate that the dose is permitted. For instance, the OCR function of the optical sensor 25 may be configured such that it is unable to perform optical character recognition of white numbers on a black background, and so be unable to read a number indicating the dialled dose until the user has operated the injection device 1 such that the dialled dose is permitted and thus that the dialled dose can be coded by the optical sensor 25. In these embodiments, the currently dialled dose is displayed only when the currently dialled dose is a permitted dose. In these embodiments, the indication that the dose is not permitted that is provided at step 406 may simply be the absence of a displayed dialled dose.

In other embodiments (not shown in the Figures), a number sleeve is provided with a permitted dose range sandwiched between non-permitted dose ranges. For instance, the surface of the number sleeve at locations corresponding to doses of 30, 60 and all values in between indicate the dose as a number that is coloured black on a white background. The surface of the number sleeve at locations corresponding to doses between 0 and 29 and from 61 upwards are indicated by a number that is coloured white on a black background. In another example, the number sleeve 19 is marked to indicate that doses of between 10 and a higher value (e.g. 20 or 40) are permitted. In particular, locations corresponding to doses of 10, 20 and all values in between indicate the dose as a number that is coloured black on a white background. Locations corresponding to doses between 0 and 9 and from 21 (or 41) upwards are indicated by a number that is coloured white on a black background.

In still further embodiments, the supplementary device 2 is operable with a number sleeve 19 that is provided with numbers only at locations corresponding to doses that are permitted. For instance, the number sleeve 19 may be provided with numbers at locations corresponding to dose values 10, 12, 14, 16, 18 and 20. Alternatively, the number sleeve 19 may be provided with numbers at locations corresponding to dose values 10, 15 and 20. In all these embodiments, the number sleeve 19 is provided with numbers that do not constitute a continuous series of dose values but instead are members of a discontinuous series. Here, the supplementary device 2 is configured such that it is unable to detect the dose except when the characteristics indicate that the dose is permitted. Here, unless a quantity of currently set dose of drug is determined, an indication that the currently set dose of drug is not a permitted dose is caused to be provided.

With these embodiments in which the dose is readable by the supplementary device 2 only at locations corresponding to a permitted dose, the user is able to determine accurately the dialled dose only if the dialled dose is within the permitted range or if the supplementary device 2 is not installed on the injection device 1.

In addition to providing an indication that the dialled dose is not a permitted dose, the supplementary device 2 may prevent dose delivery whilst the dialled dose is not a permitted dose. This may for example be achieved with a locking mechanism as described in WO 2013/076026 A1. Some other suitable locking mechanism may be used instead.

The terms "drug" or "medicament" which are used interchangeably herein, mean a pharmaceutical formulation that includes at least one pharmaceutically active compound.

The term "drug delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again without limitation, exemplary injection devices may include, e.g., syringes, autoinjectors, injection pen devices and spinal injection systems.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des (B28-B30) human insulin; Des (B27) human insulin and Des (B30) human insulin.

Exemplary insulin derivatives are, for example, B29-N-myristoyl-des (B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin; B29-N—(N-lithocholyl-gamma-glutamyl)-des (B30) human insulin; B29-N-(ω-carboxyheptadecanoyl)-des (B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na$^+$, or K$^+$, or Ca$^{2+}$, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A drug administration apparatus comprising:
a number sleeve comprising a generally cylindrical outer surface on which are provided a sequence of numbers arranged at different locations on the surface with the sequence provided in a helix, each of the sequence of numbers relating to a drug dose, wherein the surface at locations corresponding to doses within a specific dose range and the surface at locations corresponding to doses that are outside of the specific dose range have different characteristics;
an imaging arrangement configured to provide image data representing a captured image of a portion of the sequence of numbers provided on the number sleeve at a location on the number sleeve, one of the sequence of numbers corresponding to a currently set dose of medicament; and
a processor arrangement configured to:
receive the image data representing the captured image;
process the image data representing the captured image to identify one or more optically-detectable characteristics of the number sleeve at the location; and
determine from the identified one or more optically-detectable characteristics of the number sleeve whether the currently set dose of medicament is a permitted dose.

2. The drug administration apparatus of claim 1, wherein the different characteristics include different colors for the sequence of numbers on the surface of the number sleeve.

3. The drug administration apparatus of claim 2, wherein the different colors are detectable by the human eye.

4. The drug administration apparatus of claim 1, wherein the different characteristics include different colors for the sequence of numbers on the surface of the number sleeve, and different colors for a background to the sequence of numbers on the surface of the number sleeve.

5. The drug administration apparatus of claim 4, wherein the different colors are detectable by the human eye.

6. The drug administration apparatus of claim 1, wherein the different characteristics include different colors for the sequence of numbers on the surface of the number sleeve, and wherein a color of a background to the sequence of numbers is the same for all of the sequence of numbers on the number sleeve.

7. The drug administration apparatus of claim 6, wherein the different colors are detectable by the human eye.

8. The drug administration apparatus of claim 1, wherein the different characteristics include different colors for a background to the sequence of numbers on the surface of the number sleeve.

9. The drug administration apparatus of claim 8, wherein the different colors are detectable by the human eye.

10. The drug administration apparatus of claim 1, wherein the different characteristics include different colors for a background to the sequence of numbers on the surface of the number sleeve, and wherein the color of the sequence of numbers is the same for all of the sequence of numbers on the number sleeve.

11. The drug administration apparatus of claim 10, wherein the different colors are detectable by the human eye.

12. The drug administration apparatus of claim 1, wherein the surface at the locations corresponding to the doses within the specific dose range indicates the drug dose as a number that is colored black on a white background, and the surface at the locations corresponding to the doses outside the specific dose range indicates the drug dose as a number that is colored white on a black background.

13. The drug administration apparatus of claim 1, wherein the sequence of numbers are provided on the number sleeve by printing.

14. The drug administration apparatus of claim 1, wherein the drug administration apparatus contains the medicament.

15. The drug administration apparatus of claim 1, wherein the number sleeve forms part of a drug delivery device, and wherein the imaging arrangement and the processor arrangement form part of a supplementary device, the supplementary device including an attachment mechanism for coupling the supplementary device to the drug delivery device.

16. The drug administration apparatus of claim 1, wherein the processor arrangement is further configured to:
   perform optical character recognition on the image data to determine a quantity of the currently set dose of medicament represented by one or more numbers of the sequence of numbers; and
   cause display of the quantity of the currently set dose of medicament.

* * * * *